(12) United States Patent
Okayama

(10) Patent No.: US 8,401,350 B2
(45) Date of Patent: Mar. 19, 2013

(54) OPTICAL RESONATOR, AND FLUID OPTICAL SENSOR EMPLOYING AN OPTICAL RESONATOR

(75) Inventor: Hideaki Okayama, Tokyo (JP)

(73) Assignee: Oki Electric Industry Co., Ltd., Tokyo (JP)

( * ) Notice: Subject to any disclaimer, the term of this patent is extended or adjusted under 35 U.S.C. 154(b) by 450 days.

(21) Appl. No.: 12/656,693

(22) Filed: Feb. 12, 2010

(65) Prior Publication Data

US 2010/0209045 A1 Aug. 19, 2010

(30) Foreign Application Priority Data

Feb. 13, 2009 (JP) ................................. 2009-030741

(51) Int. Cl.
*G02B 6/26* (2006.01)
*G02B 6/34* (2006.01)
*G02B 6/42* (2006.01)
(52) U.S. Cl. ............................................ 385/32; 385/37
(58) Field of Classification Search ................ 385/2, 15, 385/24, 37, 32
See application file for complete search history.

(56) References Cited

U.S. PATENT DOCUMENTS

| | | | |
|---|---|---|---|
| 7,074,480 B2 | 7/2006 | Fukutani et al. | |
| 7,267,859 B1 | 9/2007 | Rabin et al. | |
| 7,335,514 B2 | 2/2008 | Grasso et al. | |
| 7,391,945 B2 | 6/2008 | Sugita | |
| 7,671,325 B2 * | 3/2010 | Sanders et al. | 250/227.18 |
| 2002/0018494 A1 * | 2/2002 | Vieira et al. | 372/9 |
| 2006/0165342 A1 * | 7/2006 | Pau et al. | 385/12 |
| 2007/0230529 A1 * | 10/2007 | Mochizuki | 372/46.01 |
| 2007/0230868 A1 * | 10/2007 | Miyadera et al. | 385/24 |
| 2009/0244544 A1 * | 10/2009 | Terrel et al. | 356/461 |

FOREIGN PATENT DOCUMENTS

JP 2007-183644 A 7/2007

OTHER PUBLICATIONS

Yasuo Kokubun, "High Index Contrast Optical Waveguides and Their Applications to Microring Filter Circuit and Wavelength Selective Switch", IEICE transactions on Electronics, vol. E90-C, No. 5 pp. 1O37-I045, May 2007.
Xiankai Sun et. al., "Surface-emitting circular DFB, disk-, and ring-Bragg resonator lasers with chirped gratings: a Unified theory and comparative study", Optics Express vol. 16, No. 12, pp. 915S-9164, Jun. 9, 2008.

* cited by examiner

*Primary Examiner* — Adolf Berhane
*Assistant Examiner* — Emily Pham
(74) *Attorney, Agent, or Firm* — Rabin & Berdo, P.C.

(57) ABSTRACT

There is provided an optical resonator including: N individual optical waveguide paths of line segment shape disposed in a common flat-plane so as to intersect at a single intersection region, wherein N is an integer of 2 or more; curved optical waveguide paths connecting respective portions of the optical waveguide paths that extend towards the outside from the intersection region, wherein for a first to a $2N^{th}$ optical waveguide path portions in a clockwise direction, connection is made between end portions at the opposite side to the intersection region of the $(2i-1)^{th}$ to $2i^{th}$ optical waveguide path portions, wherein i is an integer of 1 to N; and an optical coupler that couples light input or output perpendicular to the flat-plane with the optical waveguide paths, the optical coupler being formed in a region containing the intersection region where the optical waveguide paths are connected.

9 Claims, 9 Drawing Sheets

OPTICAL RESONATOR, AND FLUID OPTICAL SENSOR EMPLOYING AN OPTICAL RESONATOR

CROSS-REFERENCE TO RELATED APPLICATION

This application is based on and claims priority under 35 USC 119 from Japanese Patent Application No. 2009-030741 filed on Feb. 13, 2009, the disclosure of which is incorporated by reference herein.

BACKGROUND

1. Technical Field

The present invention relates to an optical resonator suitably applied in the optical field, and to an optical sensor used in a fluid optical sensor employing an optical resonator.

2. Related Art

Ring shaped optical resonators are being actively researched into as means to realize sharp filters with extremely high wavelength selectivity (see; for example, Documents 1 and 6 listed below). For coupling light to the ring resonator a configuration is generally adopted where, for introducing light, an optical fiber or an optical waveguide path is disposed in the near vicinity of an optical waveguide path configuring the ring optical resonator. Research is also being actively pursued into optical resonators employing photonic crystals (see, for example, Document 2).

However, precise positioning is required in both ring shaped optical resonators and optical resonators employing photonic crystals, since light must be coupled to the optical waveguide path, leading to inferior ease-of-use.

In contrast, a Fabry-Perot resonator is superior from the standpoint of ease-of-use, since spatial light can be made directly incident to the optical resonator. Recently, as an application of a Fabry-Perot resonator, an optical resonator is disclosed having a structure in which fine pores are made in a wafer, and light is made to be perpendicularly incident on, and perpendicularly emitted from, the surface of the wafer (see, for example, Documents 3 to 5).

The technology disclosed in Documents 3 to 5 has a substrate made from Si or made from Al, with fine pores formed by employing an anode oxidation method. With this technology, application as sensor of an optical resonator and a variable wavelength filter is achieved by utilizing that facts that (1) a substance can be introduced into the optical resonator through the fine pores, and (2) the equivalent refractive index of the fine pores is capable of modulation by adjusting the volume ratio of the fine pores.

Furthermore, an optical resonator is being developed with a grating of concentric circle shape that makes light perpendicularly incident to, and perpendicularly emitted from, the face on which the optical resonator is formed (see, for example, Document 2).

However, in the technology disclosed in Documents 3 to 5, when the optical resonator is a micro-element, it is difficult to secure a long enough resonator length in order that diffraction occurs. As a result thereof, the wavelength peak of emitted light emitted due to resonance unfortunately becomes broad.

Furthermore, in the optical resonator disclosed in Document 7, the period of the grating needs to be half the wavelength of the emitted light, or less, leading to accompanying difficulties in production.

Document 1: Japanese Patent Application Laid-Open (JP-A) No. 2007-183644
Document 2: U.S. Pat. No. 7,391,945
Document 3: U.S. Pat. No. 7,335,514
Document 4: U.S. Pat. No. 7,267,859
Document 5: U.S. Pat. No. 7,074,480
Document 6: Yasuo Kokubun, "High Index Contrast Optical Waveguides and Their Applications to Microring Filter Circuit and Wavelength Selective Switch", IEICE transactions on Electronics, Vol. E90-C, No. 5 pp 1037-1045, 2007 May
Document 7: Xiankai Sun et. al., "Surface-emitting circular DFB, disk-, and ring-Bragg resonator lasers with chirped gratings: a unified theory and comparative study", Optics Express Vol. 16, No. 12, pp 9155-9164, 2008, Jun. 9

SUMMARY

The present invention is made in consideration of the above circumstances. Consequently, a first objective of the present invention is to provide an optical resonator in which light is made perpendicularly incident on, and perpendicularly emitted from, a face on which the optical resonator is formed, a sufficiently long resonator length can be secured, and the optical resonator is easily manufactured. A second objective of the present invention is to provide an optical sensor for fluid body use that employs the above described optical resonator.

In order to solve the above issues, the present invention provides an optical resonator including:

N individual optical waveguide paths of line segment shape disposed in a common flat-plane so as to intersect at a single intersection region, wherein N is an integer of 2 or more;

curved optical waveguide paths connecting respective portions of the optical waveguide paths that extend towards the outside from the intersection region, wherein for a first to a $2N^{th}$ optical waveguide path portions in a clockwise direction, connection is made between end portions at the opposite side to the intersection region of the $(2i-1)^{th}$ to $2i^{th}$ optical waveguide path portions, wherein is an integer of 1 to N; and an optical coupler that couples light input or output perpendicular to the flat-plane with the optical waveguide paths, the optical coupler being formed in a region containing the intersection region where the optical waveguide paths are connected.

As a preferable exemplary embodiment of the above described optical resonator, the optical coupler is preferably a flat-plane waveguide path on which a grating is formed.

As a preferable exemplary embodiment of the above described optical resonator, the grating is preferably formed of a concentric circle shape from the center point of the intersection region.

As a preferable exemplary embodiment of the above described optical resonator, a connection portion of the optical coupler with the optical waveguide paths preferably is formed in a taper shape with a dimension, perpendicular to the light propagation direction and parallel to the flat-plane, that gradually decreases from the intersection region towards the outside.

As a preferable exemplary embodiment of the above described optical resonator, the optical waveguide path portions are preferably disposed at equal angular intervals around the intersection region.

The fluid optical sensor of the present invention employs the above described optical resonator.

The fluid optical sensor of claim may be provided on a substrate with:

the optical resonator;

a label for identifying the optical resonator;

an electrode provided to the curved optical waveguide paths for changing the resonator length;

a control circuit, connected to the electrode, and controlling voltage applied to the electrode; and a power source, connected to the control circuit and driving the electrode.

The present invention is equipped with technical features like those described above. As a result of which, an optical resonator can be provided in which light is made perpendicularly incident on, and perpendicularly emitted from, the face on which the optical resonator is formed, a sufficiently long resonator length can be secured, and the optical resonator is easily manufactured. Furthermore, a fluid optical sensor can be provided employing the above described optical resonator.

BRIEF DESCRIPTION OF THE DRAWINGS

Exemplary embodiments of the present invention will be described in detail based on the following figures, wherein.

DETAILED DESCRIPTION

Figure 1:
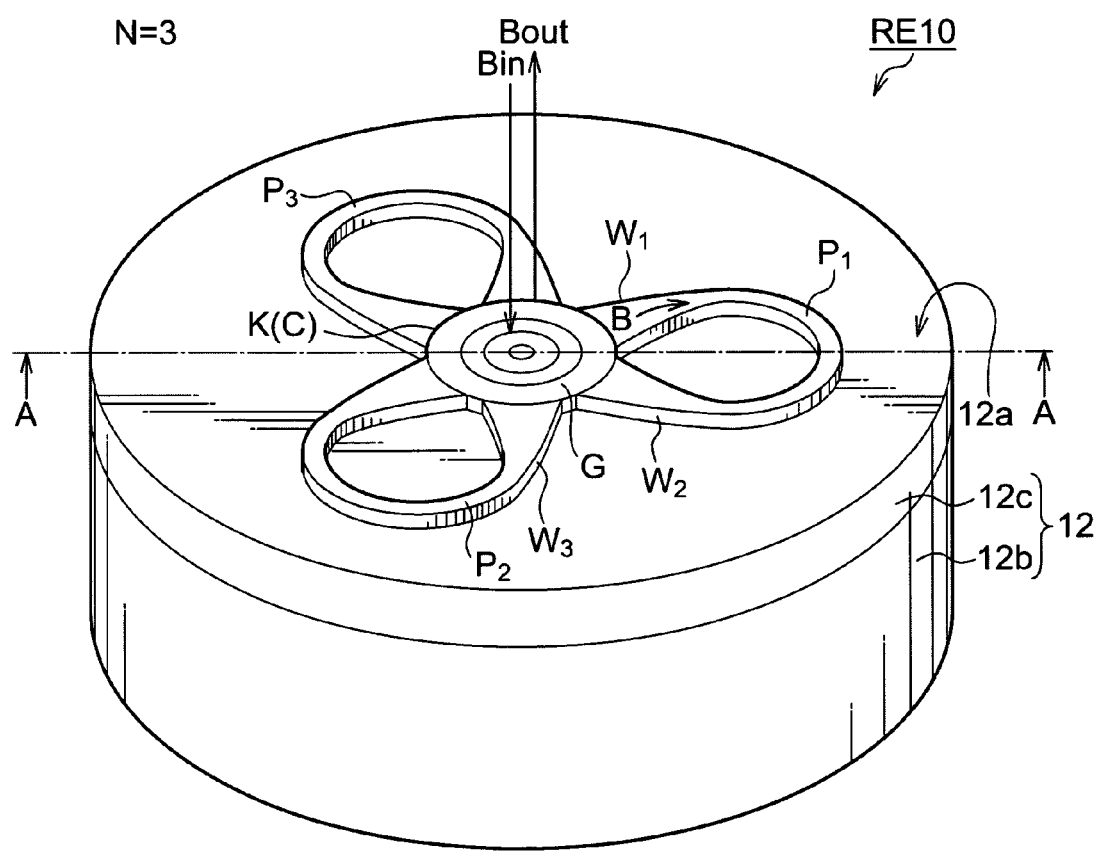
FIG. 1 is a perspective view schematically showing a structure of an optical resonator for N=3.

Explanation follows of exemplary embodiments of the present invention, with reference to the drawings. Each of the figures is a representation of the shape, size and disposition relationships of each relevant part of the configuration, at a schematic level enabling understanding of the present invention. Explanation follows next of preferable configuration examples of the present invention, however the materials of the relevant parts of the configurations, and numerical conditions are simply preferable examples thereof. Consequently, the present invention is note limited by any of the exemplary embodiments below. In each of the figures, common relevant parts of the configuration are allocated the same reference numerals, and explanation thereof is abbreviated.

First Exemplary Embodiment

Explanation follows regarding an optical resonator of a first exemplary embodiment, with reference to FIG. 1 to FIG. 6.

(A) When N is a Given Number.

First, an outline explanation follows of the most general case of an optical resonator RE provided with N optical waveguide paths (N being an integer of 2 or more). In the following explanation, for understanding purposes, reference should be made as appropriate to an optical resonator RE 10 (N=3) of FIG. 1, an optical resonator RE 20 and optical resonator RE 30 (N=2) of FIG. 5A and FIG. 5B, and an optical resonator RE 40 (N=4) of FIG. 6. In the following explanation, "optical resonator RE" will be used when referring in general to the optical resonators RE 10, RE 20, RE 30, and RE 40 having their individual specific values of N.

The optical resonator RE is equipped with N optical waveguide paths $W_1$ to $W_N$, curved optical waveguide paths $P_1$ to $P_i$, and a light coupler K. The N optical waveguide paths $W_1$ to $W_N$ are of line segment shape, disposed in a common first main face 12a (flat-plane) and intersecting at a single intersection region C. Where the respective portions of the optical waveguide paths $W_1$ to $W_N$ that extend towards the outside from the intersection region C are referred to clockwise as a first optical waveguide path segment $RW_1$ to a 2Nth optical waveguide path segment $RW_{2N}$, the curved optical waveguide paths $P_1$ to $P_i$ connect together end portions $RW_{2i-1}E$ and $RW_{2i}E$ that are at the opposite end to that of the intersection region C on the $(2i-1)^{th}$ optical waveguide path segment $RW_{2i-1}$ and the $(2i)^{th}$ optical waveguide path segment $RW_{2i}$ (wherein i is an integer from 1 to N). The light coupler K couples the light Bin and the light Bout, input and output perpendicular to the first main face 12a, with the optical waveguide paths $W_1$ to $W_N$, and the light coupler K is formed in region containing the intersection region C where the optical waveguide paths $W_1$ to $W_N$ are connected.

(B) When N=3

(B1) Overall Structure

Figure 2:
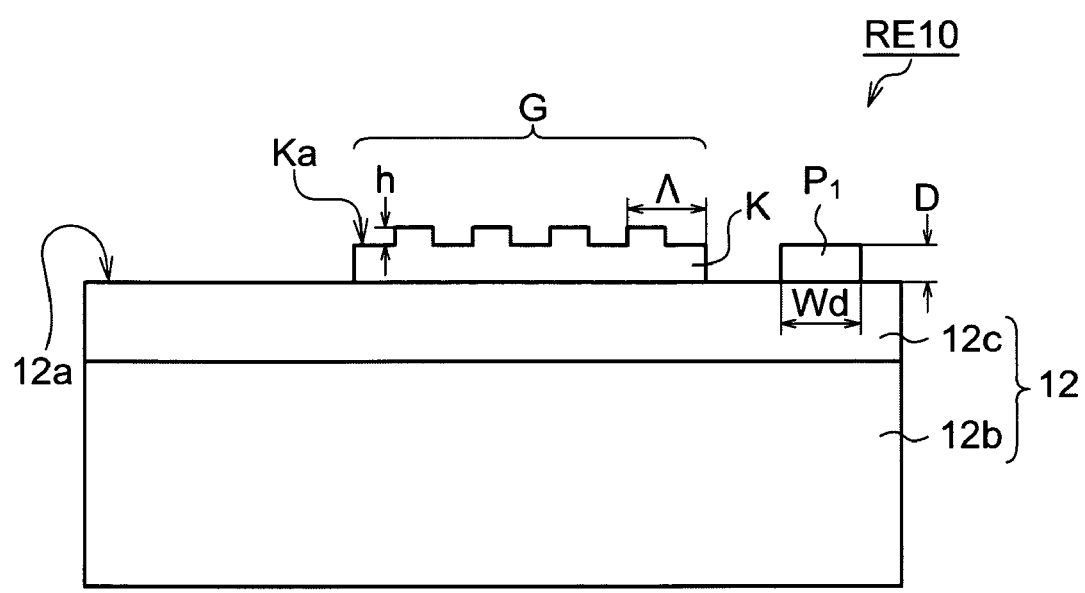
FIG. 2 is a cross-section taken on line A-A of FIG. 1.
Figure 3:
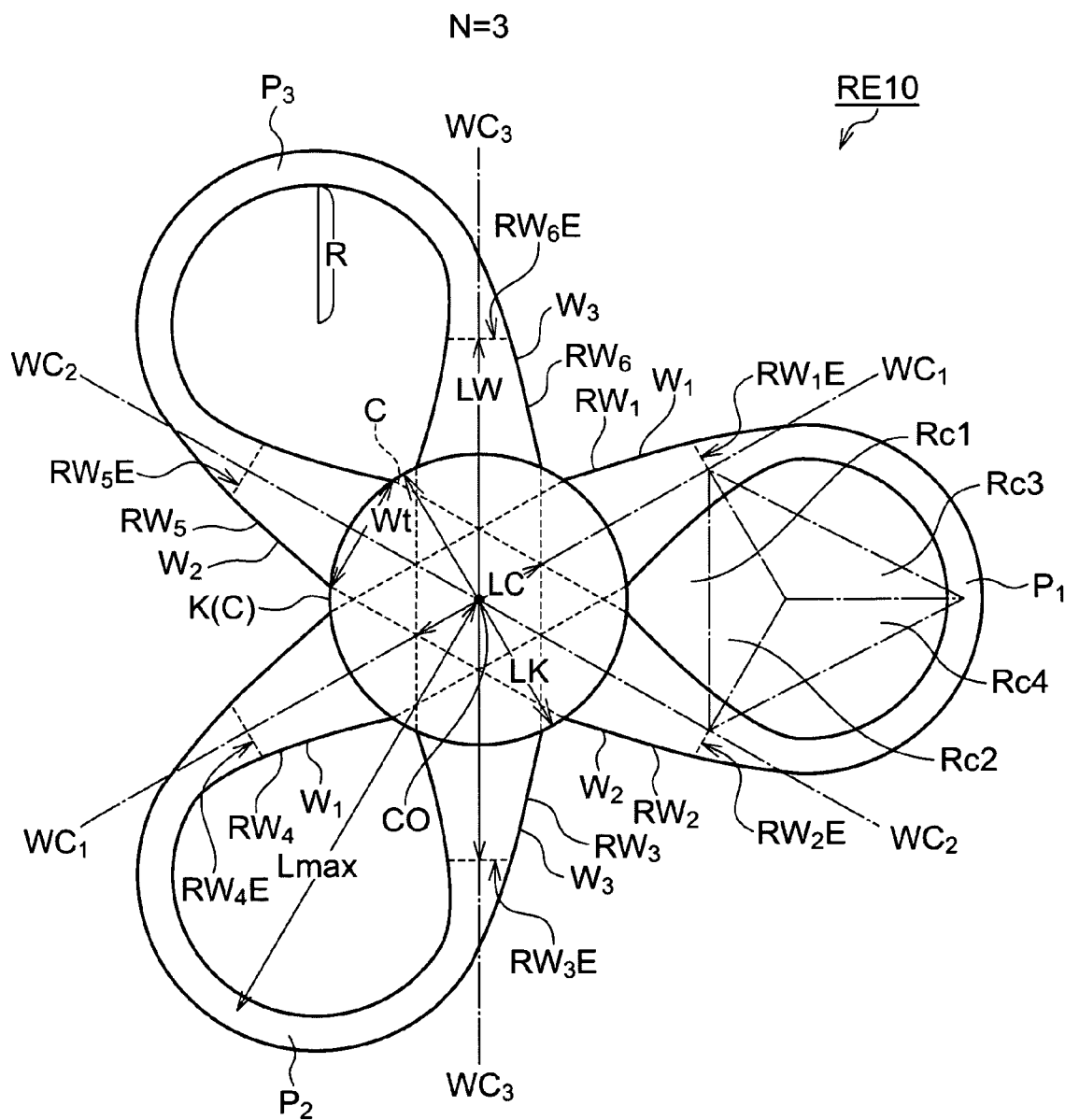
FIG. 3 is an enlarged plan view of an optical resonator for N=3.

Explanation follows of the optical resonator RE 10 equipped with three optical waveguide paths (N=3), with reference to FIG. 1 to FIG. 3.

FIG. 1 is a perspective view schematically showing a structure of an optical resonator. FIG. 2 is a cross-section taken on line A-A of FIG. 1. FIG. 3 is an enlarged plan view of the optical resonator. Note that the grating grooves are omitted from illustration in FIG. 3 in order to avoid confusion.

As shown in FIG. 1 and FIG. 3, the optical resonator RE 10 is formed on a substrate 12. More precisely, the optical resonator RE 10 is formed on a flat-plane provided to the substrate 12, namely formed on the first main face 12a of the substrate 12. The substrate 12 is described later.

The optical resonator RE 10 is configured with three optical waveguide paths $W_1$ to $W_3$, and three individual curved optical waveguide paths $P_1$ to $P_3$, and a light coupler K.

The optical waveguide paths $W_1$ to $W_3$ are of line segment shape, and are disposed so as to intersect at the single intersection region C, within the common first main face 12a (flat-plane).

The curved optical waveguide paths $P_i$ are segments connecting the portions of the optical waveguide paths $W_1$ to $W_3$ that extend toward the outside from the intersection region C. Where there are clockwise first to sixth (=2N) optical waveguide path segments $RW_1$ to $RW_6$, connection is made between the $(2i-1)^{th}$ optical waveguide path segment $RW_{2i-1}$ and the $(2i)^{th}$ optical waveguide path segments $RW_{2i}$; (wherein i is an integer from 1 to 3), at end portions $RW_{2i-1}E$ and $RW_{2i}E$ at the opposite ends to those of the intersection at the intersection region C.

The light coupler K couples light Bin and light Bout, input and output perpendicular to the first main face 12a, to the optical waveguide paths $W_1$ to $W_3$, and is formed in a region containing the intersection region C where the optical waveguide paths $W_1$ to $W_3$ are connected.

The three optical waveguide paths $W_1$ to $W_3$, the three individual curved optical waveguide paths $P_1$ to $P_3$ and the light coupler K are all optical waveguide paths, and are all integrally formed from the same material. Namely, the material configuring the optical resonator RE 10 preferably is, for example, a material having a refractive index of 3 or above and, for example, TiO, ZnO or $Ta_2O_5$ can be employed therefor. In the example shown of the present exemplary embodiment, the material configuring the optical resonator RE 10 is Si, having a refractive index of 3.5. A more detailed description will be given later, but briefly, the three optical waveguide paths $W_1$ to $W_3$, the curved optical waveguide paths $P_1$ to $P_3$ and the length of the light coupler K measured perpendicularly from the first main face 12$a$ (referred to below as the thickness) are formed with equivalent values, without local variations.

Detailed explanation follows of each relevant part of the configuration of the optical resonator RE 10.

(B2) Optical Waveguide Path

As shown in FIG. 3, the optical waveguide paths $W_1$ to $W_3$ are channel optical waveguide paths, extending in a straight line (segment) over a given length, and extending within the first main face 12$a$ so as to intersect at the single intersection region C. The optical waveguide paths $W_1$ to $W_3$ are integrally connected to the circular disk shaped light coupler K provided in a region containing the intersection region C. Both end portions of the optical waveguide paths $W_1$ to $W_3$, these being the end portions $RW_1E$ to $RW_6E$, are connected together by the curved optical waveguide paths $P_1$ to $P_3$ according to a fixed rule, described below. The light coupler K and the curved optical waveguide paths $P_1$ to $P_3$ are also described below.

The central point of the intersection region C is denoted CO, and a central axis $WC_1$ of the optical waveguide path $W_1$, a central axis $WC_2$ of the optical waveguide path $W_2$ and a central axis $WC_3$ of the optical waveguide path $W_3$ all intersect at the central point CO. Furthermore, the optical waveguide paths $W_1$ to $W_3$ are disposed at equal angular intervals around the intersection region C. Namely, the intersection angles at the intersection region C of the central axis $WC_1$ with the central axis $WC_2$, the central axis $WC_2$ with the central axis $WC_3$, and the central axis $WC_3$ with the central axis $WC_1$, are the same as each other. In the example shown of the present exemplary embodiment, the angles formed on the acute side between the central axis $WC_1$ to central axis $WC_3$ are all 60°.

In the example shown of the present exemplary embodiment, the optical waveguide paths $W_1$ to $W_3$ are formed with an overall length LW, in other words are formed with lengths relating to the light propagation direction that are the same each other. In addition, the central points of the optical waveguide paths $W_1$ to $W_3$ each align with, each other and intersect at the central point CO. Here, "central point" indicates the point at ½ of the overall length LW of the optical waveguide paths $W_1$ to $W_3$.

Detailed explanation follows at feature (B6), but briefly, the overall length LW of the optical waveguide paths $W_1$ to $W_3$ in the example shown of the present exemplary embodiment is preferably made, for example, about 4.6 μm.

The shape of a lateral cross-section of the optical waveguide paths $W_1$ to $W_3$ taken perpendicular to the light propagation direction is formed in a rectangular shape. In the example shown of the present exemplary embodiment, the width of the optical waveguide paths $W_1$ to $W_3$ at the portions connected to the light coupler K, namely the length perpendicular to the light propagation direction and parallel to the first main face 12$a$, is formed in a taper shape so as to gradually get smaller on progression from the intersection region C towards the outside. Namely, the plan-view shape of the portions of each of the optical waveguide paths $W_1$ to $W_3$ projecting out from the light coupler K are formed substantially as equilateral triangle shapes, with two sloping sides that are symmetrically disposed about the central axes $WC_1$ to $WC_3$ that act as axes of symmetry. Sometimes below, the portions of the optical waveguide paths $W_1$ to $W_3$ that project out from the light coupler K will simply be referred to as "taper portions". The reason why the taper portions are provided is in order to reduce the loss due to diffraction at the connection portions in the light propagating in the optical resonator RE 10.

The thickness D of the optical waveguide paths $W_1$ to $W_3$ measured perpendicular to the first main face 12$a$ is preferably set so that light propagating in the optical waveguide paths $W_1$ to $W_3$ becomes single-mode light. In the example shown of the present exemplary embodiment, it is known that when the optical resonator RE 10 is formed from Si, for light of wavelength in the 1.3 to 1.6 μm range, the light propagating in the optical waveguide paths $W_1$ to $W_3$ can be made single-mode light by making the thickness D 0.3 μm or less. More specifically, in the example shown of the present exemplary embodiment the thickness D is set at 0.3 μm. By setting the thickness D at 0.3 μm, light of wavelength 0.88 μm in a vacuum can be made to propagate in the optical waveguide paths $W_1$ to $W_3$ as single-mode light.

(B3) Curved Optical Waveguide Paths

The curved optical waveguide paths $P_1$ to $P_3$ are channel optical waveguide paths formed in arc shapes having a constant radius of curvature R, connecting both end portions $RW_1E$ to $RW_6E$ of the optical waveguide paths $W_1$ to $W_3$ in the first main face 12$a$ according to a fixed rule. Explanation of this fixed rule follows, with reference to FIG. 3.

Now part regions of each of three (N=3) of the optical waveguide paths $W_1$ to $W_3$, with the intersection region C as the dividing point, will be considered separately, two part regions at a time. These "part regions" will now be referred to as "light waveguide path segments". The three (N=3) optical waveguide paths $W_1$ to $W_3$ are divided into a total of six individual (2N individual) light waveguide path segments. For convenience these will be referred to, clockwise, as first to sixth optical waveguide path segments $RW_1$ to $RW_6$. The end portions at the opposite end of the first to sixth optical waveguide path segments $RW_1$ to $RW_6$ to that of the intersection region C, namely the free ends thereof, are referred to as $RW_1E$ to $RW_6E$. The first to sixth optical waveguide path segments $RW_1$ to $RW_6$ will be distinguished between using identification number i (i=1 to 3 (=N)).

When doing so, the first to the third curved optical waveguide paths $P_1$ to $P_3$ connect together the end portions $RW_{2i-1}E$ and $RW_{2i}E$ of the $(2i-1)^{th}$ optical waveguide path segment $RW_{2i-1}$ and the $(2i)^{th}$ optical waveguide path segment $RW_{2i}$. In other words, when i=1, the curved optical waveguide path $P_1$ connects together the end portions $RW_1E$ to $RW_2E$ of the first and the second optical waveguide path segments $RW_1$ to $RW_2$. When i=2, the curved optical waveguide path $P_2$ connects together the end portions $RW_3E$ to $RW_4E$ of the third and the fourth optical waveguide path segments $RW_3$ to $RW_4$. When i=3, the curved optical waveguide path $P_3$ connects together the end portions $RW_5E$ to $RW_6E$ of the fifth and the sixth optical waveguide path segments $RW_5$ to $RW_6$.

The curved optical waveguide paths $P_1$ to $P_3$ connect together each of the optical waveguide paths $W_1$ to $W_3$ based on a rule such as this. By so doing, the optical resonator RE 10 is formed in an endless shape by the optical waveguide paths $W_1$ to $W_3$, the curved optical waveguide paths $P_1$ to $P_3$, and the light coupler K, namely in a loop shape.

The radius of curvature R of the curved optical waveguide paths $P_1$ to $P_3$ is an important value that determines the loss of light propagating in the optical resonator RE 10. This is because in the curved portions of the curved optical waveguide paths $P_1$ to $P_3$, the radius of curvature R can be the cause of deviation from conditions of total internal reflection in light propagation, leading to leakage of propagating light to outside of the curved optical waveguide paths $P_1$ to $P_3$ (curvature loss) occurring.

It is known that when Si is employed as the material of the curved optical waveguide paths $P_1$ to $P_3$, if the radius of curvature R is set at 1 μm or greater, it is possible to sufficiently suppress curvature loss to a level suitable for application in practice. Therefore, in the example shown of the present exemplary embodiment, the radius of curvature R of the curved optical waveguide paths $P_1$ to $P_3$ is preferably, for example, about 1 μm.

As shown in FIG. 2, the lateral cross-section shapes of the curved optical waveguide paths $P_1$ to $P_3$ taken perpendicular to the light propagation direction are, in the example shown of the present exemplary embodiment, formed as equal rectangular shapes. In a similar manner to with the optical waveguide paths $W_1$ to $W_3$, the cross-sectional dimensions of the curved optical waveguide paths $P_1$ to $P_3$ are preferably set such that light propagation becomes single-mode light.

Specifically, the thickness D of the curved optical waveguide paths $P_1$ to $P_3$ is preferably, for example, set to 0.3 μm, and the length Wd in a direction perpendicular to the light propagation direction and parallel to the first main face 12a (referred to below as the "width") is preferably set to 0.3 μm. By setting the cross-sectional dimensions of the curved optical waveguide paths $P_1$ to $P_3$ to these values, light of wavelength 0.88 μm in a vacuum can be made to propagate within the curved optical waveguide paths $P_1$ to $P_3$ as single-mode light.

(B4) Light Coupler

The light coupler K is a flat-plane optical waveguide path of circular disk shape, formed with a grating G on the surface Ka. The center point of the outer peripheral circle of the light coupler K and the central point CO of the intersection region C coincide with each other. The light coupler K functions to couple incident light Bin that is incident perpendicular to the first main face 12a with the optical waveguide paths $W_1$ to $W_3$, and functions to emit, as emission light Bout, light resonated within the optical resonator RE 10, emitting perpendicular to the first main face 12a (see FIG. 2 and FIG. 3).

The light coupler K is provided in a region containing the intersection region C. "A region containing the intersection region C" here means that the diameter LK of the light coupler K is both greater or equal to the maximum diameter LC of the intersection region C, and also a value that is the same as or less than the overall length LW of the optical waveguide paths $W_1$ to $W_3$ (LC≦LK≦LW). Since the diameter LK of the light coupler K is set to such a value, the light coupler K overlaps with portions of the optical waveguide paths $W_1$ to $W_3$. This overlap region is provided with a grating G, described below.

A more detailed explanation is given under (B6), however briefly, in the example shown of the present exemplary embodiment, the diameter LK of the grating G is preferably, for example, about 2 μm.

The thickness D of the light coupler K measured perpendicular to the first main face 12a is preferably set such that light propagating in the light coupler K becomes single-mode light. When the optical resonator RE 10 is formed from Si, as in the example shown of the present exemplary embodiment, it is known that, for light of wavelength in the range from 1.3 μm to 1.6 μm, light propagating in the light coupler K can be made to be single-mode light by setting the thickness D to 0.3 μm or less. More specifically, in the example shown of the present exemplary embodiment the thickness D is about 0.3 μm.

The grating G formed on the surface Ka of the light coupler K is configured from plural adjacent grooves and projections, disposed as concentric circles with equal period Λ (separation interval) from the central point CO towards the outside.

The period Λ of the grating G is preferably set as $\Lambda = \lambda/N_{eff}$, wherein $N_{eff}$ is the equivalent refractive index encountered by light propagating in the optical waveguide paths $W_1$ to $W_3$, and is the wavelength of this light in a vacuum. By setting such a value for the period Λ, the incident light of wavelength λ incident onto the optical resonator RE 10 in a direction perpendicular to the first main face 12a can be coupled to the light coupler K, and therefore to the optical resonator RE 10, and converted into light propagating within the optical resonator RE 10.

Note that period Λ is about twice the size of the period of the grating described in Document 7. In this manner, as a result of making the period Λ of the light coupler K larger than the grating of Document 7, the optical resonator RE 10 in the present exemplary embodiment can be manufactured more easily than the grating of Document 7.

The height h (FIG. 2) of in the thickness direction of the grooves and projections of the grating G is related to the resonance intensity of light in the optical resonator RE 10. More precisely, the smaller the height h, the smaller the coupling effect of the incident light on the optical resonator RE 10. This means that the resonance intensity of the light in the optical resonator RE 10 increases, in other words the intensity of the emission light Bout increases.

When light of about 1 μm in wavelength λ is made to resonate by the optical resonator RE 10, in practice, in order to obtain sufficient intensity of emission light Bout, the height h in the thickness direction is preferably, for example, set at about 30 nm, and the period Λ is preferably, for example, set at about 380 nm.

In the example shown of the present exemplary embodiment, explanation is given of a case in which the grating G is a blazed diffraction grating, however the grating G may be a refractive index modulation diffraction grating.

(B5) Substrate

In the example shown of the present exemplary embodiment, the substrate 12 is a circular shaped parallel sided flat plate, configured with a base plate 12b and cladding layer 12c stacked on the base plate 12b.

In the example shown of the present exemplary embodiment, the base plate 12b is, for example, made from Si. The cladding layer 12c is formed from a material having a smaller refractive index than the material configuring the optical resonator RE 10. In the example shown of the present exemplary embodiment the material of the cladding layer 12c is, for example, made from $SiO_2$.

When the base plate 12b is formed from a material with a high refractive index of three or more times that of cladding layer 12c, the cladding layer 12c is preferably formed with a thickness of 1 μm or greater, in order to prevent light from leaking out from the optical resonator RE 10 into the base plate 12b. Furthermore, when the base plate 12b is formed from a material of low refractive index, such as, for example, glass, quartz, resin or the like, the cladding layer 12c can be omitted.

(B6) Optical Resonator Design Parameters

A detailed explanation follows of the dimensions of each portion of the optical resonator RE 10, with reference to FIG. 3.

As already explained at (B3), in the optical resonator. RE 10, the value of the radius of curvature R of the curved optical waveguide paths $P_1$ to $P_3$ is an important value that determines the loss of light propagating of the optical resonator RE 10 overall. Therefore, the overall length LW of the optical waveguide paths $W_1$ to $W_3$ is preferably designed based on to the radius of curvature R.

The overall length LW of the optical waveguide paths $W_1$ to $W_3$ is derived from the radius of curvature R as set out in the following.

Consider the triangle Rc1 in FIG. 3, having the central axis $WC_1$ and the central axis $WC_2$, corresponding to the first and second optical waveguide path segments $RW_1$ and $RW_2$, as two sloping sides, and the central point CO as the apex. In Rc1 here the apex angle corresponding to the central point CO is 60°. The lengths of the two sloping sides corresponding to the first and second optical waveguide path segments $RW_1$ and $RW_2$ are each LW/2. Consequently, triangle Rc1 is an equilateral triangle.

Furthermore, when the end portions $RW_1E$ and $RW_2E$ of the first and second optical waveguide path segments $RW_1$ and $RW_2$ are connected together by the curved optical waveguide path $P_1$ of constant radius of curvature R, then isosceles triangles Rc2 to Rc4 are formed, each having an apex angle of 120°.

As a result, the length of the two sloping sides of the triangle Rc1, namely the length LW/2 of the first and second optical waveguide path segments $RW_1$ and $RW_2$, can be uniquely derived geometrically from the radius of curvature R.

The relationship between the radius of curvature R and LW/2 can be represented by the following Equation (1), irrespective of the value of N, namely irrespective of the number of the optical waveguide paths $W_1$ to $W_N$.

$$LW/2=(2R/3^{0.5})/\sin(2\pi/(4N)) \quad (1)$$

Note that Equation (1) only holds when the optical waveguide path segments $RW_1$ to $RW_{2N}$ are disposed at equal angle intervals around the intersection region C.

By substituting N=3 into Equation (1), the overall length LW of the optical waveguide paths $W_1$ to $W_3$ of the optical resonator RE 10 shown in FIG. 3 is derived as: $LW=(4R/3^{0.5})/\sin(\pi/6)$.

When the radius of curvature R of the curved optical waveguide paths is equal, then from Equation (1), it can be seen that as the number N of the optical waveguide paths increases, the overall length LW of the optical waveguide paths can be increased. Conversely, it can be seen that the radius of curvature R may be increased in order to make the overall length LW of the optical waveguide paths sufficiently long.

Furthermore, the maximum dimension $L_{max}$ of the optical resonator RE 10, namely the maximum separation distance between the central point CO and the curved optical waveguide paths $P_1$ to $P_3$, is given geometrically by the following Equation (2), using the radius of curvature R.

$$L_{max}=(LW/2)\cos(2\pi/(4N))+1.5R=\{(\sqrt[2]{3}^{0.5})/\tan(2\pi/(4N))+1.5\}R \quad (2)$$

By substituting N=3 in Equation (2), the maximum dimension $L_{max}$ of the optical resonator RE 10, in the optical resonator RE 10 shown in FIG. 3, is derived as $L_{max}=1.5+3^{0.5}2LW/2=3R$.

According to Equation (2), it can be seen that as the radius of curvature R gets smaller, and the number N of the optical waveguide paths gets smaller, the maximum dimension $L_{max}$ of the optical resonator RE 10, namely the size, can be made smaller.

Furthermore, the diameter LK of the light coupler K is derived according to the following.

From the diameter of the light coupler K being LK, the length of the circumference of the circle made by the light coupler K is $KL\pi$. There are 2N individual optical waveguide path segments $RW_1$ to $RW_{2N}$ connected to the light coupler K. Therefore, in the maximum case, the width Wt of the taper at the connection portion of the light coupler K and the waveguide path segments $RW_1$ and $RW_{2N}$ is $KL\pi/2N$.

However, the diffraction width Diff of the light propagating in the light coupler K is known to be given by the following Equation (3).

$$\text{Diff}=\lambda G/(N_{eff}Wt)=2N\lambda(N_{eff}\pi) \quad (3)$$

Resulting from the above, for Diff/Wt, the proportion of light loss due to refraction at the connection portions of the light coupler K and the waveguide path segments $RW_1$ and $RW_{2N}$ is derived from the following Equation (4).

$$\text{Diff}/Wt=4N^2\lambda(N_{eff}\pi^2KL) \quad (4)$$

Therefore, an appropriate value can be set for the diameter KL of the light coupler K by considering the light loss proportion Diff/Wt and the number of the optical waveguide paths N.

(B7) Operation

Explanation follows regarding the operation of the optical resonator RE 10, with reference to FIG. 1.

The incident light Bin, incident onto the optical resonator RE 10 perpendicular to the first main face 12a, is converted by the action of the grating G provided to the light coupler K into propagating light B that propagates parallel to the first main face 12a within the light coupler K, serving as a flat-plane optical waveguide path. The propagating light B is thereby coupled to the optical waveguide paths $W_1$ to $W_3$. The propagating light B that is coupled to the optical waveguide paths $W_1$ to $W_3$ propagates in the curved optical waveguide paths $P_1$ to $P_3$, and is re-coupled to the light coupler K.

In the light coupler K, the propagating light B, of proportional intensity determined by the coupling coefficient of the grating G, is externally emitted from the optical resonator RE 10 as emission light Bout, perpendicular to the first main face 12a. Due to a similar process to that described above, a portion of the incident light Bin is coupled to the light coupler K.

The propagating light B that has not been externally emitted merges with a component part of the incident light Bin coupled to the light coupler K, and repeats circulation along the path of: the optical waveguide path $W_1$ to $W_3 \to$ curved optical waveguide path $P_1$ to $P_3 \to$ optical waveguide path $W_1$ to $W_3 \to$ light coupler K.

In this process, the intensity of the propagating light B gradually increases, and is subjected to wavelength selection by resonance. Namely, only the propagating light B of wavelengths whose phase match after one revolution of the path light coupler K $\to$ optical waveguide paths W1 to W3 $\to$ curved optical waveguide paths P1 to P3 $\to$ optical waveguide paths W1 to W3 $\to$ light coupler K meet the conditions required for resonance, and increase in intensity with each revolution.

When the intensity of the propagating light B has become sufficiently intense it is observed as emission light Bout emitted perpendicular to the first main face 12a. In the present exemplary embodiment, an example is shown where the emission light Bout is emitted in the direction in which the incident light Bin is incident, however if the thickness of the substrate 12 is sufficiently thin, the emission light Bout is also emitted from the back face of the substrate 12, at the opposite side to that of the first main face 12a.

Figure 4:
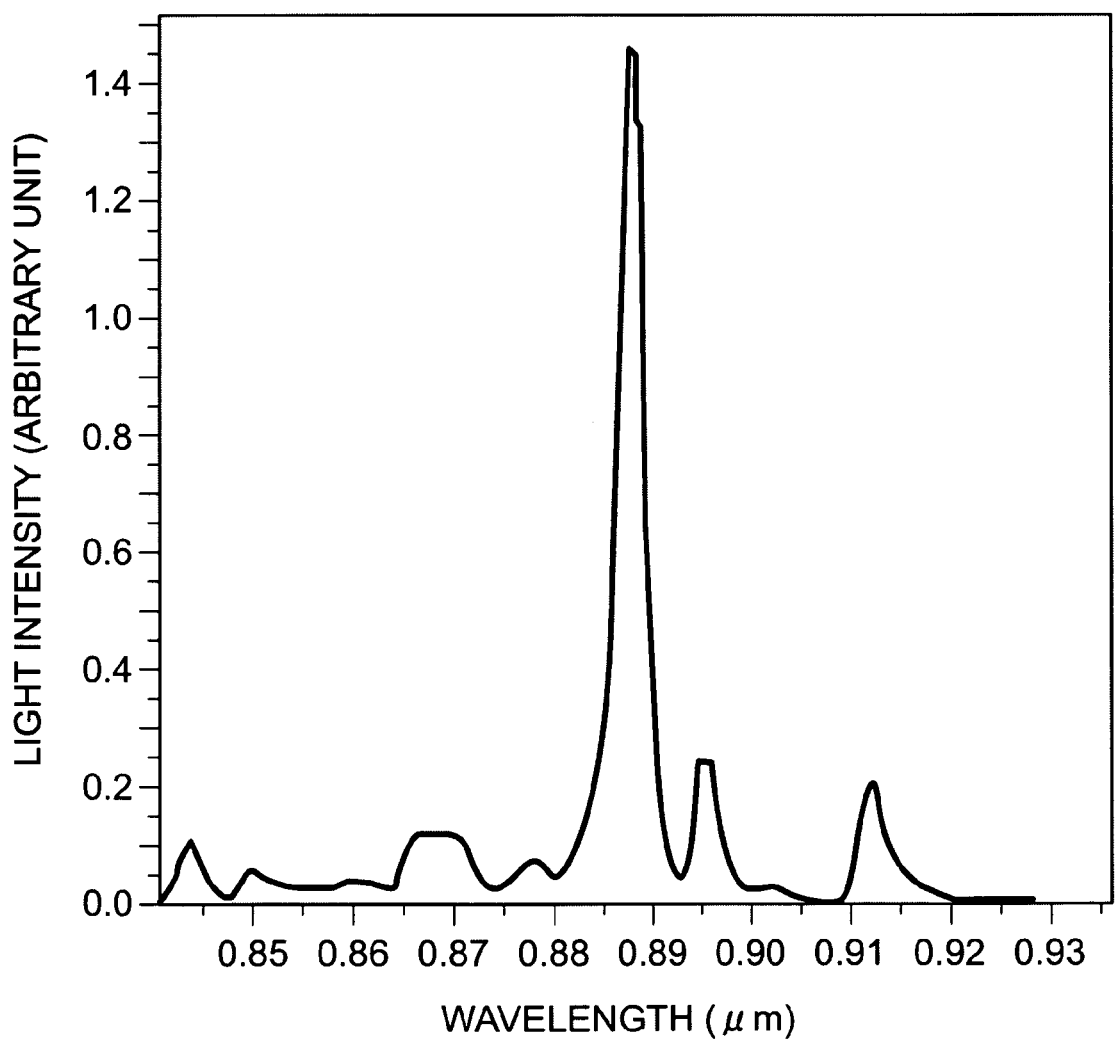
FIG. 4 is a graph showing results of a simulation on an optical resonator for N=3.

Explanation follows of an example of the operation of the optical resonator RE 10, with reference to FIG. 4. FIG. 4 is a graph showing results of a simulation on the optical resonator RE 10, and shows the optical resonator RE 10 operating as intended. In FIG. 4, the vertical axis represents the optical intensity (in arbitrary units) of the emission light Bout, and the horizontal axis shows the wavelength (μm) of the emission light Bout.

The simulation was performed by a three dimensional Finite Difference Time Domain method (FDTD method). The simulation was executed on the optical resonator RE 10 of the dimensions already explained in (B1) to (B6). During the simulation, in order to reduce the computational load, the surroundings of the optical resonator RE 10 were assumed to be entirely the atmosphere. The material configuring the optical resonator RE 10 was assumed to be Si with a refractive index of 3.5. Furthermore, the incident light Bin was assumed to be white light of wavelengths from 0.84 to 0.94 μm, with the incident light Bin assumed to be incident perpendicular to the surface Ka of the light coupler K.

As shown in FIG. 4, a sharp resonance peak was observed at about 0.887 μm. Namely, it is clear that resonance light of about 0.887 μm can be excited in the optical resonator RE 10.

(C) When N=2

Figure 5A:
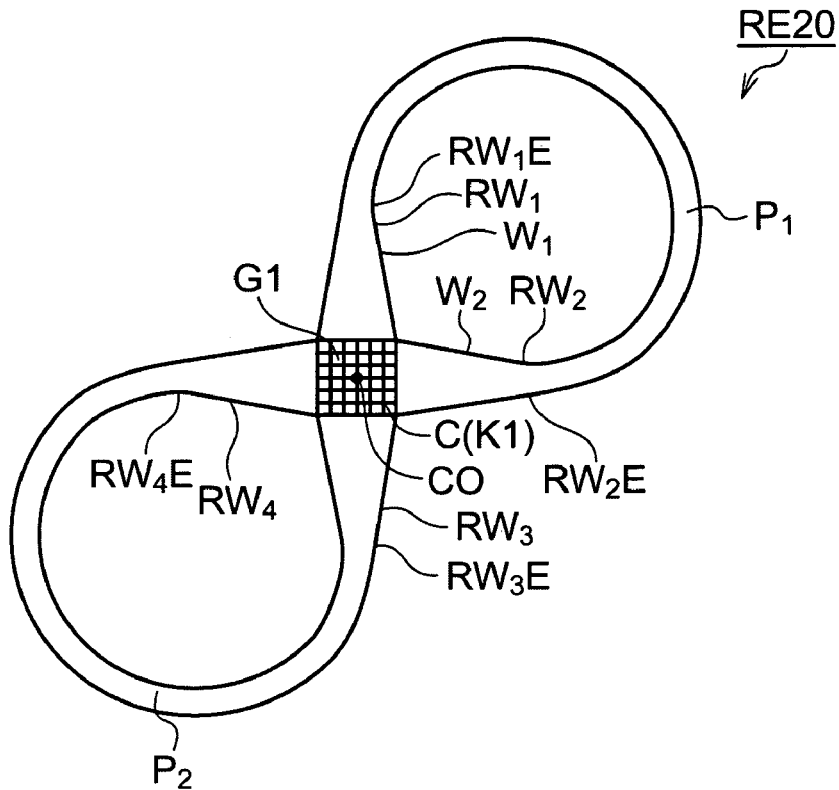
FIG. 5A is a plan view schematically showing the structure of an optical resonator of a first exemplary embodiment in a case where N=2.
Figure 5B:
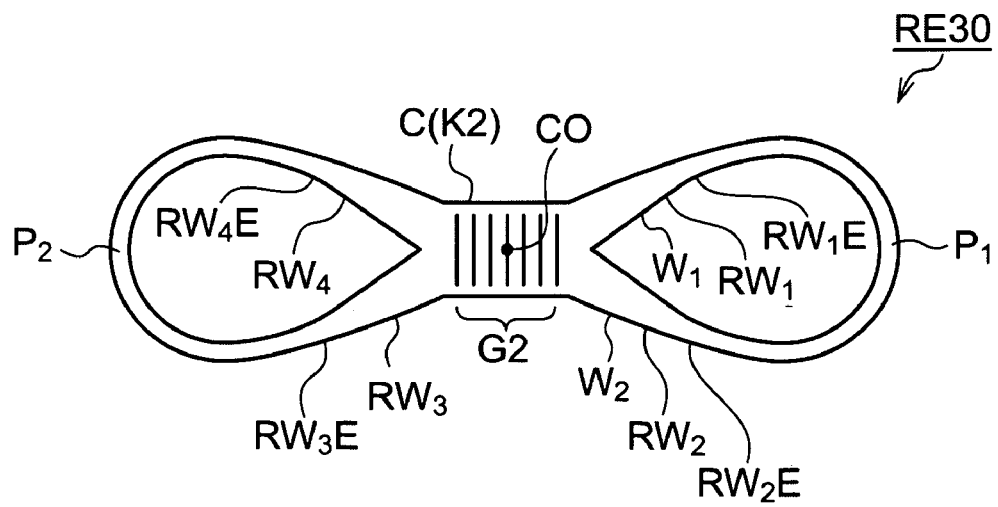
FIG. 5B is a plan view schematically showing the structure of an optical resonator of a second exemplary embodiment in a case where N=2.

Explanation follows of a case of an optical resonator equipped with two (N=2) optical waveguide paths, with reference to FIG. 5A to FIG. 5B.

FIG. 5A is a plan view schematically showing a structure of an optical resonator of a first exemplary embodiment for N=2. FIG. 5B is a plan view schematically showing a structure of an optical resonator of a second exemplary embodiment for N=2. In FIG. 5A and FIG. 5B, common parts of the configuration to FIG. 1 to FIG. 3 are allocated the same reference numerals, and explanation thereof is abbreviated. In FIG. 5A and FIG. 5B, the substrate 12 is also omitted in the drawings. Namely, while the flat-plane on which the optical resonator is disposed is not shown in FIG. 5A and FIG. 5B, it should be understood that the optical resonator RE 20 and optical resonator RE 30 extend on a flat-plane (referred to below as the first main face) equivalent to that formed by the surface of the paper on which the figures are drawn.

(C1) First Exemplary Embodiment

Explanation follows regarding the optical resonator RE 20 of the first exemplary embodiment in which N=2, with reference to FIG. 5A. The optical resonator RE 20 is configured similarly to the optical resonator RE 10 of FIG. 1, except in the two points that (1) N=2, and (2) the structure of the light coupler K1. These two points of difference will now be explained in sequence.

(C2) N=2

The optical resonator RE 20 is equipped with two (N=2) optical waveguide paths $W_1$ to $W_2$, curved optical waveguide paths $P_1$ to $P_i$ (wherein i is an integer from 1 to 2), and a light coupler K1. The two optical waveguide paths $W_1$ to $W_2$ are of line segment shape disposed in a common flat-plane and intersecting at a single intersection region C. Where the respective portions of the optical waveguide paths $W_1$ to $W_2$ that extend out towards the outside from the intersection region C are referred to clockwise as the first to fourth (=2N) optical waveguide path segments $RW_1$ to $RW_4$, the curved optical waveguide paths $P_1$ to $P_i$ connect together end portions $RW_{2i-1}E$ and $RW_{2i}E$ that are at the opposite end to that of the intersection region C on the $(2i-1)^{th}$ optical waveguide path segment $RW_{2i-1}$ and the $(2i)^{th}$ waveguide path segment $RW_{2i}$. The light coupler K1 couples the light Bin and the light Bout, input and output perpendicular to the first main face, with the optical waveguide paths $W_1$ to $W_2$, and the light coupler K1 is formed in region containing the intersection region C where the optical waveguide paths $W_1$ to $W_2$ are connected. The connection portions here between the light coupler K1 and the optical waveguide paths $W_1$ to $W_2$ are formed in a taper shape with a dimension, perpendicular to the light propagation direction and parallel to the flat-plane, that gradually decreases from the intersection region C towards the outside. Furthermore, the optical waveguide path segments $RW_1$ to $RW_4$ are disposed at equal angle (=90°) intervals around the intersection region C. Furthermore, a grating G1 is formed to the light coupler K1 in order to input and output light to and from the outside.

(C3) Structure of the Light Coupler K1

The light coupler K1 provided to the optical resonator RE 20 has a flat-plane optical waveguide path of a square shape in plan view, and a grating G1 is formed on the top face thereof. The grating G1 has an equal period Λ in both the left-right direction shown on the paper, and in the up-down direction shown on the paper, configured from plural adjacent grooves and protrusions (lattice grooves) disposed at equal intervals. In other words, as shown in FIG. 5A, the lattice grooves of the grating G1 are formed vertically and horizontally, intersecting at right angles, in a draught-board pattern.

The reason the lattice grooves intersect at right angles in this manner is in order to increase the usable efficiency of the light. Namely, both the TE wave and the TM wave components included in the incident light Bin can be coupled to the optical resonator RE 20 by making the lattice grooves intersect at right angles.

(C4) Second Exemplary Embodiment

Explanation follows regarding the optical resonator RE 30 of the first exemplary embodiment in which N=2, with reference to FIG. 5B. The optical resonator RE 30 is configured similarly to the optical resonator RE 10 of FIG. 1, except for the three points that (1) N=2, (2) the structure of the light coupler K2 are different from those of the optical resonator RE 10 of FIG. 1, and also (3) the intersection angle of the optical waveguide paths $W_1$ and $W_2$ are not equal. These three points of difference will now be explained in sequence.

(C5) N=2

Except in that the optical waveguide path segments $RW_1$ to $RW_4$ are disposed at non-equal angular intervals around the intersection region C, the explanation is the same as the explanation of (C2) and so is abbreviated here.

(C6) Structure of the Light Coupler K2

The light coupler K2 provided to the optical resonator RE 30 has a flat-plane optical waveguide path of a rectangular shape in plan view, and a grating G2 is formed on the top face thereof. The grating G2 is equipped with the already explained grooves and protrusions (lattice grooves) of equal period Λ, disposed along the length direction of the rectangle. The lattice grooves extend parallel to each other along the short length direction of the rectangle.

(C7) Difference in Intersection Angle of the Optical Waveguide Path

When N=2, since the number of the optical waveguide paths $W_1$ and $W_2$ is small, the optical waveguide paths $W_1$ and $W_2$ can be comparatively freely placed. In the optical resonator RE 30 shown in FIG. 5B, the size of two sets of opposing pairs of apex angles of the optical waveguide paths $W_1$ and $W_2$ are different from each other. The light coupler K2 is disposed so that the pair of opposing apex angles on the acute angle side are present extending along the length direction.

(D) When N=4

Figure 6:
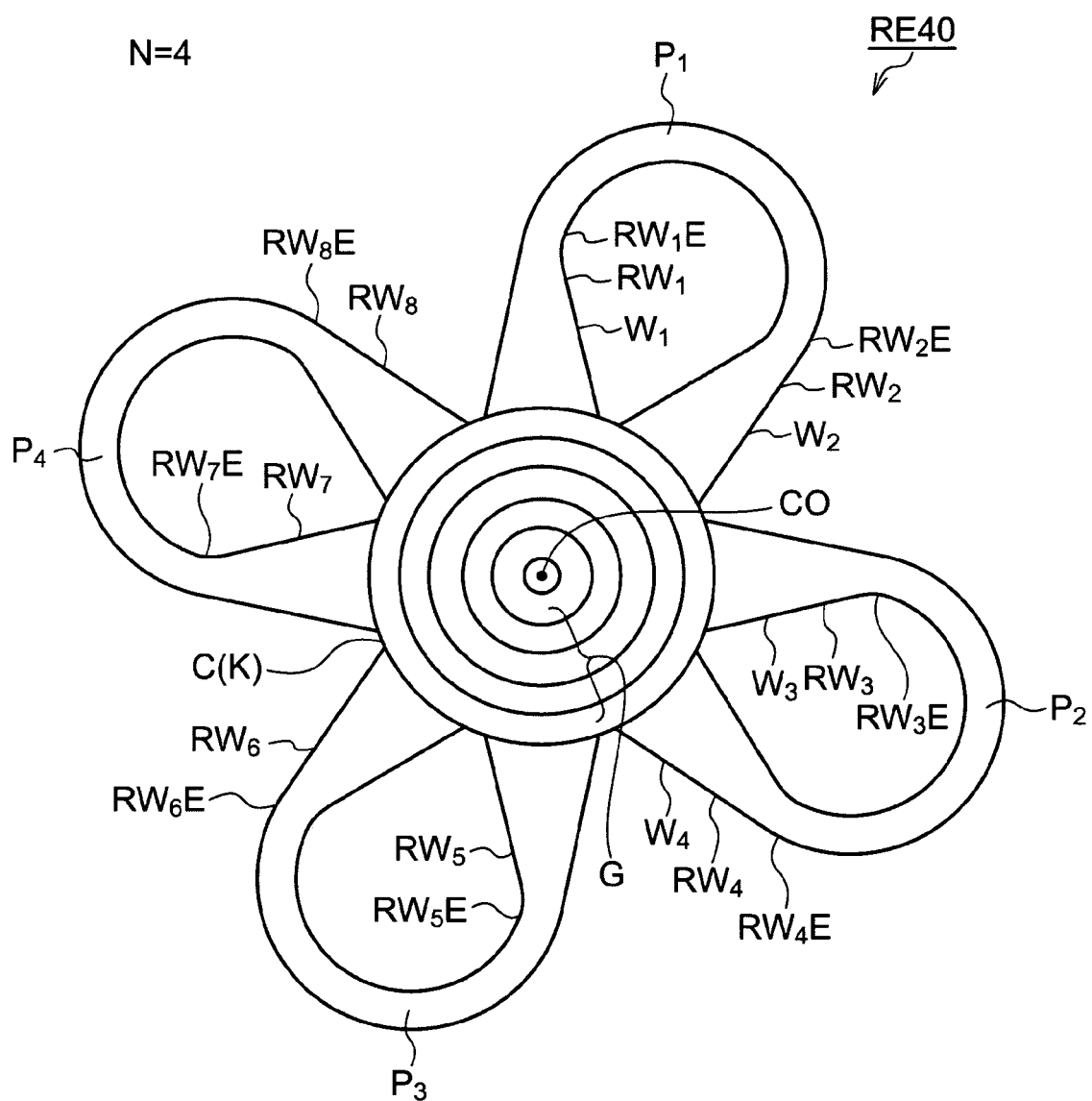
FIG. 6 is a plan view schematically showing the structure of an optical resonator for N=4.

Explanation follows of an optical resonator equipped with four (N=4) optical waveguide paths, with reference to FIG. 6.

FIG. 6 is a plan view schematically showing the structure of an optical resonator when N=4.

Note that in FIG. 6, those configuration parts that are common to those of FIG. 1 to FIG. 3 are allocated the same reference numerals, and explanation thereof is abbreviated. Furthermore, the substrate 12 is omitted from the drawing in FIG. 6. Namely, while the flat-plane on which the optical resonator is disposed is not shown in FIG. 6, it should be understood that the optical resonator RE 40 extends on a flat-plane (referred to below as the first main face) formed by the surface of the paper on which the figure is drawn.

The optical resonator RE 40 is configured similar to that of the optical resonator RE 10 of FIG. 1, except in the point that (1) N=4.

Namely, the optical resonator RE 40 is equipped with four (N=4) optical waveguide paths $W_1$ to $W_4$, curved optical waveguide paths $P_1$ to $P_i$ (wherein i is an integer from 1 to 4), and a light coupler K. The four optical waveguide paths $W_1$ to $W_4$ are of line segment shape disposed in a common flat-plane and intersecting at a single intersection region C. Where the respective portions of the optical waveguide paths $W_1$ to $W_4$ that extend out towards the outside from the intersection region C are referred to clockwise as the first to eighth (=2N) optical waveguide path segments $RW_1$ to $RW_8$, the curved optical waveguide paths $P_1$ to $P_i$ connect together end portions $RW_{2i-1}E$ and $RW_{2i}E$ that are at the opposite end to that of the intersection region C on the $(2i-1)^{th}$ optical waveguide path segment $RW_{2i-1}$ and the $(2i)^{th}$ optical waveguide path segment $RW_{2i}$. The light coupler K couples the light Bin and the light Bout, input and output perpendicular to the first main face, with the optical waveguide paths $W_1$ to $W_4$, and the light coupler K is formed in region containing the intersection region C where the optical waveguide paths $W_1$ to $W_4$ are connected. The connection portions here between the light coupler K and the optical waveguide paths $W_1$ to $W_4$ are formed in a taper shape with a dimension, perpendicular to the light propagation direction and parallel to the flat-plane, that gradually decreases from the intersection region C towards the outside. Furthermore, the optical waveguide path segments $RW_1$ to $RW_8$ are disposed at equal angle (=45°) intervals around the intersection region C. Furthermore, a grating G is formed to the light coupler K in order to input and output light to and from the outside. The grating G is formed in a concentric circular shape out from the central point CO of the intersection region C.

(E) Effect (E1) The optical resonator RE of the present invention can ensure a sufficiently long resonator length by increasing the number of optical waveguide paths $W_1$ to $W_N$. As a result, emission light Bout having a narrow wavelength distribution can be obtained.

(E2) The optical resonator RE of the present invention, as already explained, has a period Λ of the grating G, G1, G2 that is about twice the period of the grating in Document 7. Consequently, a larger tolerance can be made in the manufacturing precision required when manufacturing the optical resonator RE, and in particular the grating G, G1, G2. Consequently, the optical resonator RE is more easily manufactured than the optical resonator of Document 7.

(F) Remarks (F1) In the present exemplary embodiment explanation has been given of a case where the incident light Bin is incident onto the optical resonator RE perpendicular to the first main face 12a. However, the incident light Bin is required simply to have a light component that is perpendicular to the first main face 12a. Namely, the incident light Bin may be incident at a sloping angle to the first main face 12a.

Second Exemplary Embodiment

Figure 7:
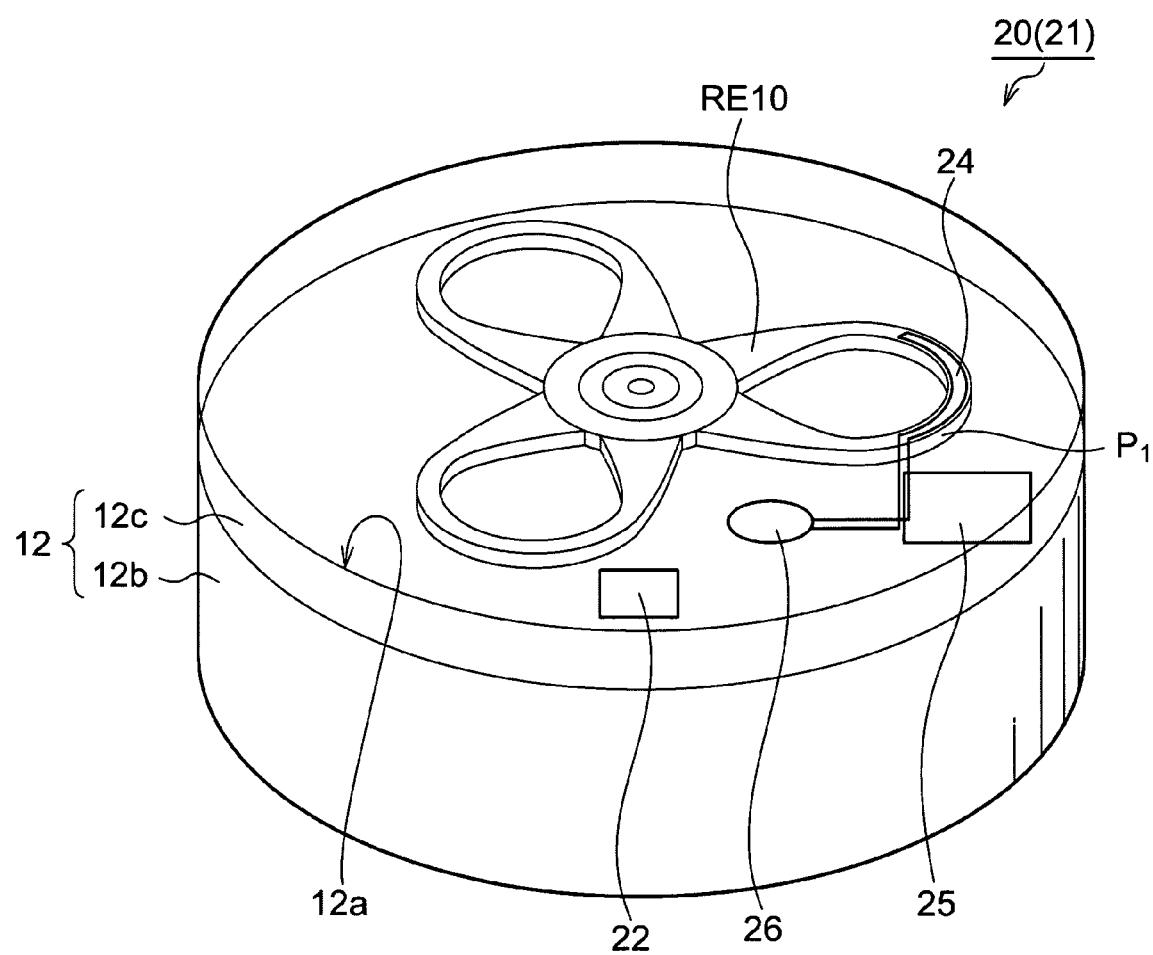
FIG. 7 is a perspective view of a fluid optical sensor.
Figure 8:
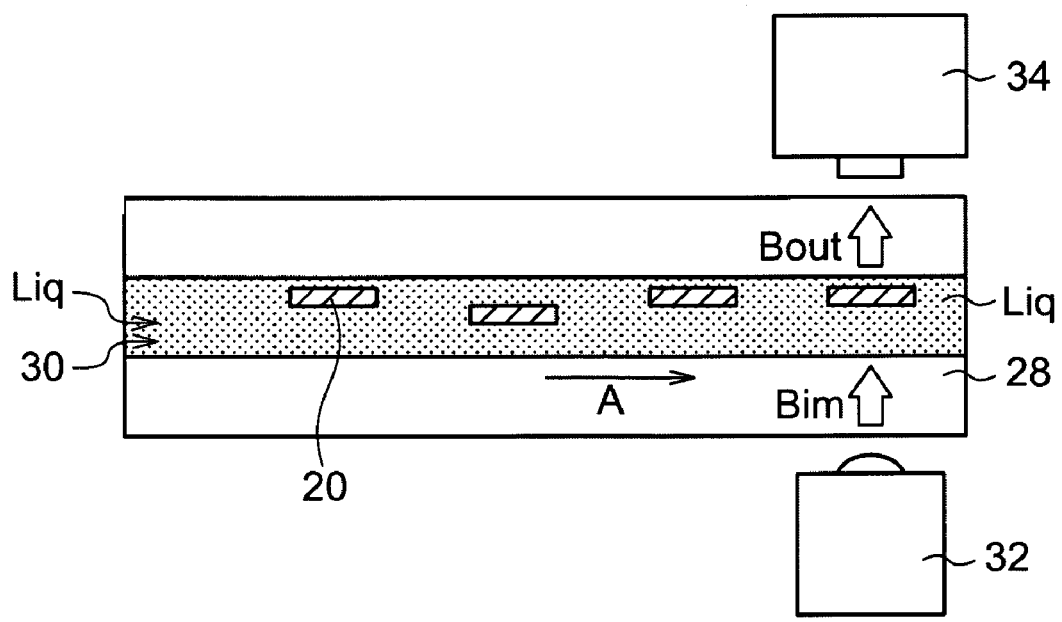
FIG. 8 is a schematic diagram to accompany explanation of operation states of a fluid optical sensor.

Explanation follows regarding a optical sensor for fluids of a second exemplary embodiment, with reference to FIG. 7 and FIG. 8.

FIG. 7 is a perspective view of a fluid optical sensor 20. FIG. 8 is a schematic diagram to accompany explanation of the operation sate of the fluid optical sensor. Note that parts of the configuration in FIG. 8 that are similar to those of FIG. 1 to FIG. 3 are allocated the same reference numerals and explanation thereof is abbreviated.

As shown in FIG. 7, the fluid optical sensor 20 is equipped with a substrate 12, and an optical modulation section 21 provided on a first main face 12a of the substrate 12.

The optical modulation section 21 is equipped with: an optical resonator RE 10; a label 22 for identifying the optical resonator RE 10; an electrode 24 provided on a curved optical waveguide path $P_1$; a control circuit 25, connected to the electrode 24, for controlling the voltage applied to the electrode 24; and a power supply 26, connected to the control circuit 25, for controlling driving of the electrode 24.

In the example shown of the present exemplary embodiment, the label 22 is preferably, for example, a barcode formed using micro-manufacturing technology, with a different pattern disposition for each one of the fluid optical sensors 20. By reading in the barcode using, for example, a microscope or the like, individual of the fluid optical sensors 20 can be identified.

The electrode 24 is a metallic film formed on the surface of the curved optical waveguide path $P_1$. The refractive index of the curved optical waveguide path $P_1$ is changed by changing the voltage applied to the electrode 24, resulting in the resonator length of the optical resonator RE 10 changing. Due thereto, the resonance wavelength of the optical resonator RE 10 can be changed. The electrode 24 can be formed by application of known semiconductor fabrication processing technology.

The control circuit 25 is electrically connected to the electrode 24 by patterned wiring on the first main face 12a of the substrate 12. The control circuit 25 acts to, control the voltage applied to the electrode 24. The control circuit 25 is configured as an Integrated Circuit (IC) formed by application of known semiconductor fabrication processing technology. The control circuit 25 receives power supplied by the power supply 26, and changes the size of voltage applied to the electrode 24 with a specific voltage application pattern, according to a program incorporated into the IC. The configuration of the IC is known, and explanation thereof will be omitted since it is not directly relevant to the thrust of the present invention.

The power supply 26 is electrically connected to the control circuit 25 by patterned wiring on the first main face 12a of the substrate 12. The power supply 26 acts to supply power to the control circuit 25 and the electrode 24. In the example shown of the present exemplary embodiment, the power supply 26 preferably, for example, is formed as a solar cell. Note that such a solar cell is manufactured by application of known semiconductor fabrication processing technology.

Explanation continues regarding the measurement principle of the fluid optical sensor 20. Evanescent light propagating in the optical resonator RE 10 configuring the fluid optical sensor 20 dissipates, by a small amount, out from the optical waveguide path to the external portion where the fluid body to be measured is present. Consequently, if the refractive index of the fluid body (liquid body or gaseous body) present externally changes, the equivalent refractive index encountered by the light changes. Corresponding to this change, the resonance conditions of the optical resonator RE 10 also change by a small amount, and the wavelength of the emission light Bout changes by a small amount. By monitoring the change Δλ in the wavelength of the emission light Bout, it is possible to evaluate the change in the refractive index of the fluid body present surrounding the fluid optical sensor 20.

Explanation follows of a specific example of an application of the fluid optical sensor 20, with reference to FIG. 8.

FIG. 8 shows fluid optical sensors 20 flowing downstream in the direction of arrow A, along with a fluid body to be measured Liq, in a micro-flow-path 30 formed in a substrate 28. A light source 32 is provided below the micro-flow-path 30 as an irradiation section that irradiates incident light Bin onto the fluid optical sensors 20. A detector 34 is provided above the micro-flow-path 30, at a position that faces towards the light source 32, as a detection section that receives emission light Bout emitted after passing through the fluid optical sensors 20.

By configuring in such a manner, changes to the refractive index of the fluid body to be measured Liq flowing in the flow in the micro-flow-path 30 can be measured according to the principle explained above.

According to the fluid optical sensor 20 of the present exemplary embodiment, any change to the refractive index of the fluid body to be measured Liq can be detected in real time.

Furthermore, since in the fluid optical sensor 20, the control circuit 25 can change the voltage applied to the electrode 24 in a specific pattern, changes in the refractive index relating to emission light Bout of plural wavelengths can be detected.

In the present exemplary embodiment, explanation is given of a case of the fluid optical sensor 20 measuring the refractive index of a fluid body to be measured. However, the fluid optical sensors 20 are capable of application in light absorption rate measurement.

Furthermore, in the present exemplary embodiment, a case is explained in which the power supply 26 is a solar cell. However, the power supply 26 may, for example, be configured as a microwave antenna, and power supplied by irradiating microwaves from outside onto the microwave antenna.

Note that the fluid optical sensors 20 may be further provided, for example, with power sources, circuits, microwave antennae, and the like, in order to perform input and output of data to and from the outside.

In the example shown of the present exemplary embodiment, explanation is given of a case in which the optical resonator RE 10 is applied as the fluid optical sensor 20. However, the optical resonator simply needs the optical waveguide paths $W_1$ to $W_N$ to be two or more, and application can be made to the fluid optical sensor 20 irrespective of the value of N.

Furthermore, in the example shown of the present exemplary embodiment, a case is explained in which the optical resonator RE is applied as the fluid optical sensor 20. However, various embodiments may be used as long as the optical resonator is one that can be input with and emit light perpendicular to the first main face of a substrate.

Third Exemplary Embodiment

Figure 9:
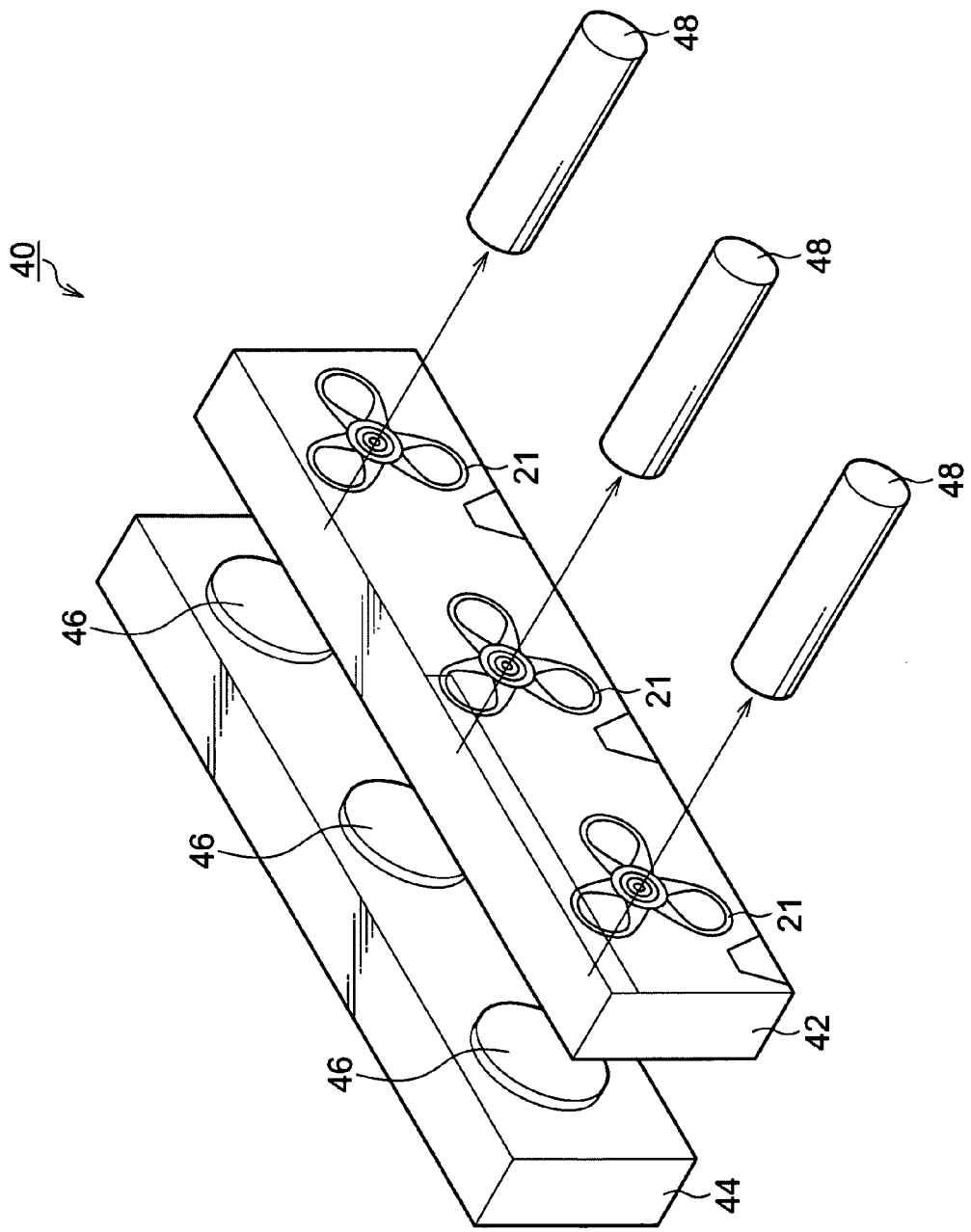
FIG. 9 is a perspective view schematically showing the structure of a parallel optical communication device.

Explanation follows of a parallel optical communication device of a third exemplary embodiment, with reference to FIG. 9. FIG. 9 is a perspective view schematically showing the structure of a parallel optical communication device. Configuration parts in FIG. 9 that are similar to those in FIG. 1 to FIG. 3 and FIG. 8 are allocated to the same reference numerals, and explanation thereof is abbreviated.

A parallel optical communication device 40 is equipped with plural surface emitting lasers 46, . . . 46, plural optical modulation sections 21, . . . 21, and plural optical fibers 48, . . . 48.

The surface emitting lasers 46, . . . 46 are disposed in a straight line at equal intervals on a common rectangular shaped parallel sided flat plate substrate 44. As is known, the surface emitting lasers 46, . . . 46 emit laser light in a direction perpendicular to the surface of the substrate 44.

The optical modulation sections 21, . . . 21 are disposed in straight ling at equal intervals on a common rectangular shaped parallel sided flat plate substrate 42. The optical modulation sections 21, . . . 21 are interposed between the surface emitting lasers 46, . . . 46 and the optical fibers 48, . . . 48. More precisely, the optical modulation sections 21, . . . 21 are disposed in the propagation path of laser light output from the surface emitting lasers 46, . . . 46.

Each of the optical modulation sections 21, . . . 21 corresponds one-to-one with one of the surface emitting lasers 46, . . . 46. Namely, the laser light output from each of the individual surface emitting lasers 46, . . . 46 is output to the corresponding optical fiber 48, . . . 48, after being modulated by one of the optical modulation sections 21, . . . 21.

The parallel optical communication device 40 of the present exemplary embodiment employs the surface emitting lasers 46, . . . 46, and the optical modulation sections 21, . . . 21, and so is more easily fabricated than previously, and a decrease in device size can be achieved in comparison to previously.

In the present exemplary embodiment explanation is given of the optical resonator RE applied as the parallel optical communication device 40. However, various embodiments of the optical resonator may be employed as the parallel optical communication device 40, as long as the optical resonator can be input and can output light perpendicular to the first main face of the substrate.

What is claimed is:

1. An optical resonator comprising:
   N individual optical waveguide paths of line segment shape disposed in a common flat-plane so as to intersect at a single intersection region, wherein N is an integer of 2 or more;
   curved optical waveguide paths connecting respective portions of the optical waveguide paths that extend towards the outside from the intersection region, wherein for a first to a $2N^{th}$ optical waveguide path portions in a clockwise direction, connection is made between end portions at the opposite side to the intersection region of the $(2i-1)^{th}$ to $2i^{th}$ optical waveguide path portions, wherein i is an integer of 1 to N; and
   an optical coupler that couples light input or output perpendicular to the flat-plane with the optical waveguide paths, the optical coupler being formed in a region containing the intersection region where the optical waveguide paths are connected,
   wherein light is inputted into an input end of the optical coupler, passes through the curved optical waveguide paths, and then is outputted from an output end of the optical coupler, the input end and the output end being the same.

2. The optical resonator of claim 1, wherein the optical coupler comprises a flat-plane waveguide path formed with a grating.

3. The optical resonator of claim 2, wherein the grating is formed in a concentric circular shape from the center point of the intersection region.

4. The optical resonator of claim 1, wherein a connection portion of the optical coupler with the optical waveguide paths is formed in a taper shape with a dimension, perpendicular to the light propagation direction and parallel to the flat-plane, that gradually decreases from the intersection region towards the outside.

5. The optical resonator of claim 1, wherein the optical waveguide path portions are disposed at equal angular intervals around the intersection region.

6. An optical sensor for use in a fluid, the fluid optical sensor comprising the optical resonator of claim 1.

7. The fluid optical sensor of claim 6, provided on a substrate with:

the optical resonator;

a label for identifying the optical resonator;

an electrode provided to the curved optical waveguide paths for changing the resonator length;

a control circuit, connected to the electrode, and controlling voltage applied to the electrode; and a power source, connected to the control circuit and driving the electrode.

8. The optical resonator of claim 1, wherein the optical coupler is located at a center of the intersection region and the curved optical waveguide paths are disposed at equal angular intervals around the optical coupler.

9. The optical resonator of claim 1, wherein the optical coupler, taken from a plan view, has a circular disk shape.

* * * * *